United States Patent [19]

Menzel et al.

[11] Patent Number: 5,744,314

[45] Date of Patent: *Apr. 28, 1998

[54] PERIPLASMIC MEMBRANE-BOUND SYSTEM FOR DETECTING PROTEIN-PROTEIN INTERACTIONS

[75] Inventors: Rolf Menzel, Princeton Junction; Scott T. Taylor, West Windsor, both of N.J.

[73] Assignee: Bristol-Myers Squibb Company, Princeton, N.J.

[ * ] Notice: The term of this patent shall not extend beyond the expiration date of Pat. No. 5,521,066.

[21] Appl. No.: 642,552

[22] Filed: May 3, 1996

Related U.S. Application Data

[63] Continuation of Ser. No. 121,201, Sep. 13, 1993, Pat. No. 5,521,066.

[51] Int. Cl.$^6$ ............................. C12Q 1/02; C12N 15/12
[52] U.S. Cl. ..................... 435/7.2; 435/7.32; 435/69.7; 435/252.3; 435/252.33; 435/320.1; 435/325; 536/23.4
[58] Field of Search ..................... 435/7.32, 7.2, 435/69.7, 252.3, 252.33, 320.1, 325; 536/23.4

[56] References Cited

U.S. PATENT DOCUMENTS 4,774,182  9/1988  Szybalski ........................... 435/68

OTHER PUBLICATIONS

Miller, V. L., et. al. (1987) Cell, 48(2), 271–279.
DiRita, et., V, J., et. al. (1991)Cell 64, 29–37.
Schlessinger, J. (1988) TIBS 13, 443–447.
Stock, J.B., et. al. (1989) Microbiol. Rev. 54(4), 450–490.

*Primary Examiner*—Charles L. Patterson, Jr.
*Attorney, Agent, or Firm*—Timothy J. Gaul

[57] ABSTRACT

The present invention relates to:

(1) a fusion protein having a dimerizing domain with or without a ligand-binding region and toxR DNA-binding and hydrophobic transmembrane regions;

(2) host cells comprising the fusion protein and a nucleic acid molecule having a reporter gene operatively linked to the ctx operon, wherein dimerization (ligand-dependent or -independent) is signaled by expression of the reporter gene;

(3) a nucleic acid molecule coding for the fusion protein;

(4) an expression vector comprising a coding region for the fusion protein;

(5) a process for detecting dimer formation (ligand dependent or ligand independent) of the fusion protein, which comprises treating a culture of the host cells with a ligand, ligand mimetic, or dimerization inhibitor, and screening for expression of the reporter gene.

The present invention can be used to generate a signal from a variety of ligand-binding domains, allowing ligand binding to be indicated by a simple colorimeteric test or antibiotic resistance. The fusion proteins could include therapeutically relevant domains, so that biologically pertinent interactions can be indicated by a readily measurable signal.

29 Claims, 8 Drawing Sheets

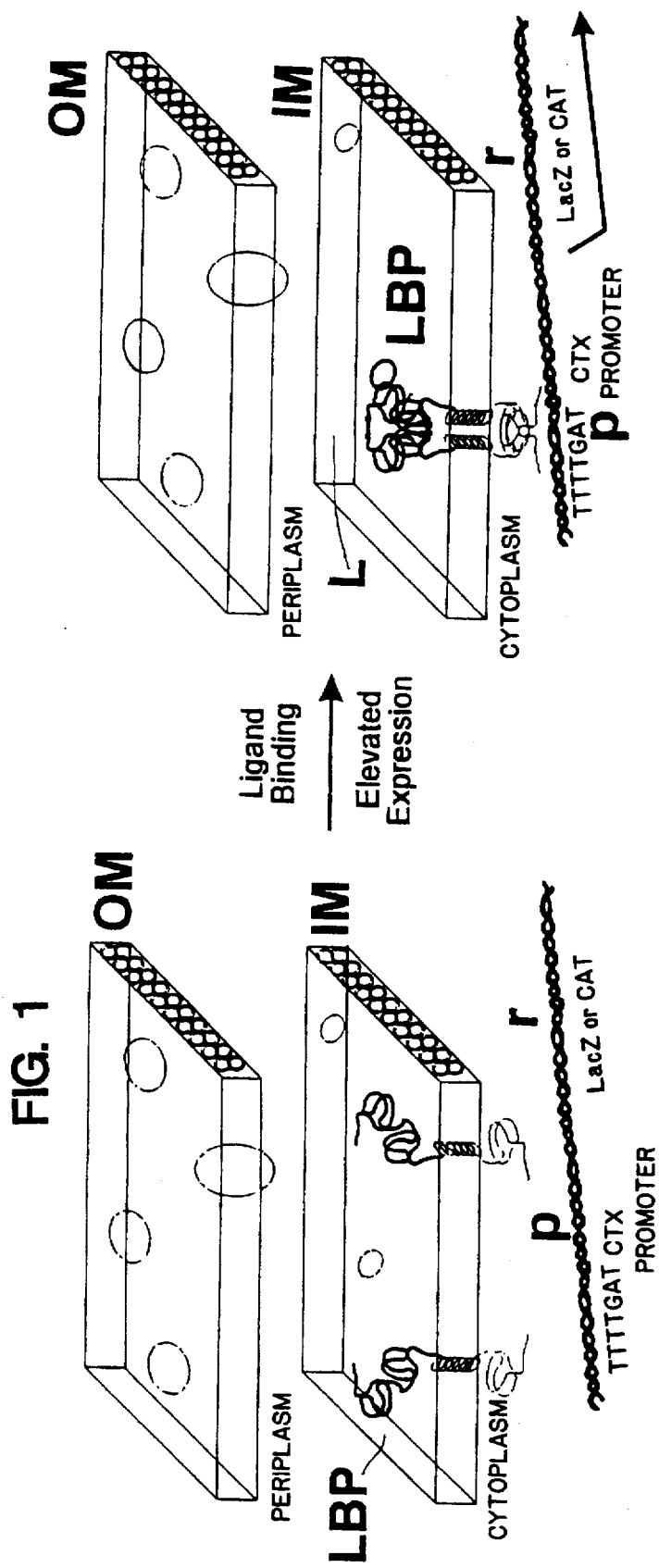

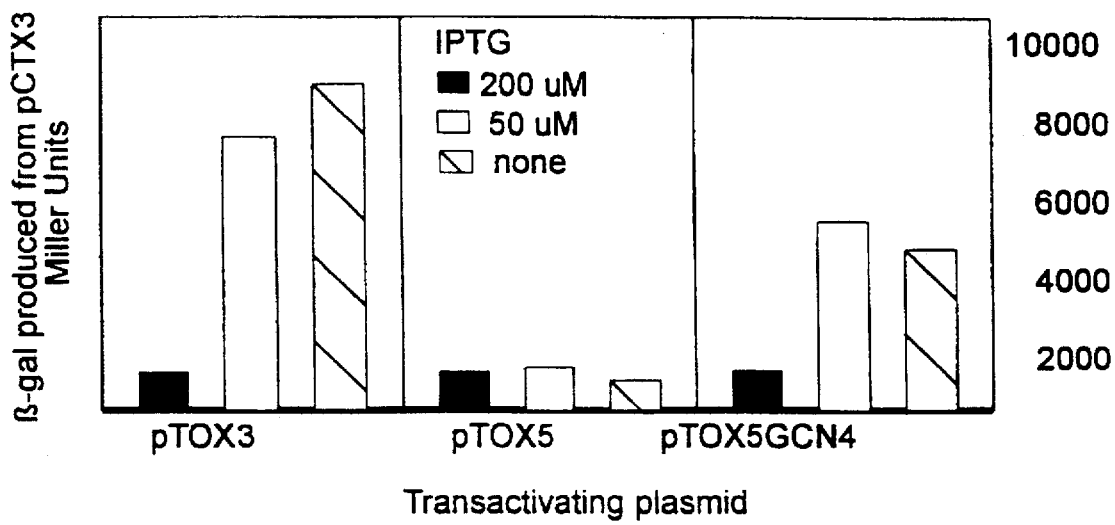

FIG. 5A

| | | LB- | LB+ | MIN- | MIN+ |
|---|---|---|---|---|---|
| +TM,DEG+ | trkC1 | 2087 | 1635 | 3519 | 2564 |
| | trkC2 | 1118 | 1391 | 1577 | 1939 |
| | trkC3 | 1454 | 4987 | 2277 | 8363 |
| | trkC4 | 1515 | 4221 | 2162 | 6817 |
| | trkC5 | 971 | 725 | 1501 | 1067 |
| | trkC6 | 798 | 3238 | 1078 | 5223 |
| | trkC7 | 891 | 881 | 1303 | 1292 |
| -TM,DEG- | trkC8 | 2322 | 1380 | 2978 | 2537 |
| | trkC9 | 777 | 643 | 1034 | 1078 |
| | trkC10 | 3267 | 3154 | 3702 | 4688 |
| | trkC11 | 1163 | 818 | 1592 | 1403 |
| | trkC12 | 1015 | 3389 | 1315 | 7263 |
| | trkC13 | 956 | 807 | 1509 | 1349 |
| | trkC14 | 2872 | 2953 | 4199 | 4307 |
| | trkC15 | 863 | 4065 | 1165 | 6804 |
| | trkC16 | 602 | 1757 | 1068 | 4775 |
| | trkC17 | 821 | 4304 | 1396 | 6771 |
| | trkC18 | 982 | 2057 | 1413 | 3214 |
| | trkC19 | 940 | 3261 | 1418 | 5283 |
| | trkC20 | 1075 | 932 | 1774 | 1503 |
| | trkC21 | 931 | 1310 | 1692 | 1939 |
| | trkC22 | 2525 | 4366 | 3069 | 6165 |
| | trkC23 | 2249 | 2445 | 2919 | 3819 |
| | trkC24 | 850 | 2751 | 1181 | 3497 |
| | trkC25 | 1391 | 1766 | 2409 | 3058 |
| | trkC26 | 898 | 3494 | 1246 | 4326 |
| -TM,DEG+ | trkC27 | 651 | 3539 | 1216 | 5655 |
| | trkC28 | 1156 | 3044 | 1659 | 3948 |
| | trkC29 | 447 | 2222 | 579 | 2013 |
| | trkC30 | 672 | 1277 | 1032 | 1435 |
| Controls | tox3 | 554 | 2443 | 903 | 4253 |
| | tox3 | 609 | 2888 | 895 | 4638 |
| | tox3 | 524 | 2818 | 920 | 4144 |
| | tox5 | 284 | 286 | 664 | 711 |
| | tox5 | 365 | 240 | 661 | 683 |
| | tox5 | 302 | 274 | 790 | 625 |

| trkC Deletion Number | Deletion Size (bp) | Deletion Endpoints in pTOXTRKC-tm |
|---|---|---|
| trkC 1 | 875 | 634 - 1509 |
| trkC 3 | 905 | 634 - 1539 |
| trkC 6 | 389 | 634 - 1023 |
| trkC 10 | 683 | 634 - 1317 |
| trkC 12 | 71 | 634 - 705 |
| trkC 14 | 347 | 639 - 986 |
| trkC 15 | 71 | 634 - 705 |
| trkC 17 | 71 | 634 - 705 |
| trkC 22 | 71 | 634 - 705 |
| trkC 23 | 407 | 634 - 1041 |

☐ trkC deletions 12,15,17,22
▭ trkC deletion 14
▭ trkC deletion 6
▭ trkC deletion 23
▭ trkC deletion 10
▭ trkC deletion 1
▭ trkC deletion 3 toxR    T.M.    trkC - T.M.
0       500     1000    1500    2000

[Chloramphenicol] µg/ml

| Strain | 0.00 | 2.50 | 5.00 | 10.00 | 20.00 | 40.00 |
|---|---|---|---|---|---|---|
| D4/pTOX3 | R | R | R | R | R | R |
| D4/pTOX5 | R | R | S | S | S | S |
| D4/pTOX5ICP35 | R | R | R | S | S | S |
| J4/pTOX3 | R | R | R | R | R | R |
| J4/pTOX5 | R | R | S | S | S | S |
| J4/pTOX5HIVINT | R | R | R | R | S | S |

D4= DH5α
J4= JM101
R= Resistant
S= Sensitive

FIG. 6C

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1105 base pairs
        ( B ) TYPE: nucleic acid
        ( C ) STRANDEDNESS: double (D) TOPOLOGY: linear (i i) MOLECULE TYPE: DNA (genomic)

(x i) SEQUENCE DESCRIPTION: SEQ ID NO:1:

| | | | | | | |
|---|---|---|---|---|---|---|
| GTGAGTGAGT | GAGTGTTGGG | ACAGGGACAT | ACTGGGACAT | TAGATGTTCG | GATTAGGACA | 60 |
| CAACTCAAAA | GAGATATCGA | TGAGTCATAT | TGGTACTAAA | TTCATTCTTG | CTGAAAAATT | 120 |
| TACCTTCGAT | CCCCTAAGCA | ATACTCTGAT | TGACAAAGAA | GATAGTGAAG | AGATCATTCG | 180 |
| ATTAGGCAGC | AACGAAAGCC | GAATTCTTTG | CTGCTGGCC | CAACGTCCAA | ACGAGGTAAT | 240 |
| TTCTCGCAAT | GATTTGCATG | ACTTTGTTTG | GCGAGAGCAA | GGTTTTGAAG | TCGATGATTC | 300 |
| CAGCTTAACC | CAAGCCATTT | CGACTCTGCG | CAAAATGCTC | AAAGATTCGA | CAAAGTCCCC | 360 |
| ACAATACGTC | AAAACGGTTC | CGAAGCGCGG | TTACCAATTG | ATCGCCCGAG | TGGAAACGGT | 420 |
| TGAAGAAGAG | ATGGCTCGCG | AAAACGAAGC | TGCTCATGAC | ATCTCTCAGC | CAGAATCTGT | 480 |
| CAATGAATAC | GCAGAATCAA | GCAGTGTGCC | TTCATCAGCC | ACTGTAGTGA | ACACACCGCA | 540 |
| GCCAGCCAAT | GTCGTGGCGA | ATAAATCGGC | TCCAAACTTG | GGGAATCGAC | TGTTTATTCT | 600 |
| GATAGCGGTC | TTACTTCCCC | TCGCAGTATT | ACTGCTCACT | AACCCAAGCC | AATCCAGCTT | 660 |
| TAAACCCCTA | ACGGTTGTCG | ATGGCGTAGC | CGTCAATATG | CCGAATAACC | ACCCTGATCT | 720 |
| TTCAAATTGG | CTACCGTCAA | TCGAACTGTG | CGTTAAAAAA | TACAATGAAA | AACATACTGG | 780 |
| TGGACTCAAG | CCGATAGAAG | TGATTGCCAC | TGGTGGACAA | ATAACCAGT | TAACGCTGAA | 840 |
| TTACATTCAC | AGCCCTGAAG | TTTCAGGGGA | AAACATAACC | TTACGCATCG | TTGCTAACCC | 900 |
| TAACGATGCC | ATCAAAGTGT | GTGAGTAGGA | TCTTGCTATG | CAAAATAGAC | ACATCGCCAT | 960 |
| GGGTATTCTT | CATAGGAAAA | CTGAAGAGCA | TCTGATCGAC | TTCACTATCA | CAGTTCCCAC | 1020 |
| GCACAGCAAT | GATCTGCTGA | GCAAACTGAT | TCAATTTTTC | AGCGACGGCT | ACAGGGTTGT | 1080 |
| ACCTTGCGGG | CCATCTAGGC | CTGCA | | | | 1105 |

(2) INFORMATION FOR SEQ ID NO:2:

(i) SEQUENCE CHARACTERISTICS:
(A) LENGTH: 843 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:2:

| | | | | | | |
|---|---|---|---|---|---|---|
| TTCCTGCAGT | GAGTGAGTGA | GTGTTGGGAC | AGGGAGATAC | TGGGACATTA | GATGTTCGGA | 60 |
| TTAGGACACA | ACTCAAAAGA | GATATCGATG | AGTCATATTG | GTACTAAATT | CATTCTTGCT | 120 |
| GAAAAATTTA | CCTTCGATCC | CCTAAGCAAT | ACTCTGATTG | ACAAAGAAGA | TAGTGAAGAG | 180 |
| ATCATTCGAT | TAGGCAGCAA | CGAAAGCCGA | ATTCTTTGGC | TGCTGGCCCA | ACGTCCAAAC | 240 |
| GAGGTAATTT | CTCGCAATGA | TTTGCATGAC | TTTGTTTGGC | GAGAGCAAGG | TTTTGAAGTC | 300 |
| GATGATTCCA | GCTTAACCCA | AGCCATTTCG | ACTCTGCGCA | AAATGCTCAA | AGATTCGACA | 360 |
| AAGTCCCCAC | AATACGTCAA | AACGGTTCCG | AAGCGCGGTT | ACCAATTGAT | CGCCCGAGTG | 420 |
| GAAACGGTTG | AAGAAGAGAT | GGCTCGCGAA | AACGAAGCTG | CTCATGACAT | CTCTCAGCCA | 480 |
| GAATCTGTCA | ATGAATACGC | AGAATCAAGC | AGTGTGCCTT | CATCAGCCAC | TGTAGTGAAC | 540 |
| ACACCGCAGC | CAGCCAATGT | CGTGGCGAAT | AAATCGGCTC | CAAACTTGGG | GAATCGACTG | 600 |
| TTTATTCTGA | TAGCGGTCTT | ACTTCCCCTC | GCAGTATTAC | TGCTCACTAA | CCCAAGCCAA | 660 |
| TCCAGCTTTA | AACCCCTAAC | GGTTGTCGAT | GGCGTAGCCG | TCAATATGCC | GAATAACCAC | 720 |

```
CCTGATCTTT    CAAATTGGCT    ACCGTCAATC    GAACTGTGCG    TTAAAAAATA    CAATGAAAAA        780

CATACTGGTG    GACTCAAGCC    GATAGAAGTG    ATTGCCACTG    GTGGCCATCT    AGGCCTGCAG        840

GAA                                                                                    843
```

( 2 ) INFORMATION FOR SEQ ID NO:3:

( i ) SEQUENCE CHARACTERISTICS:
        ( A ) LENGTH: 145 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
AACAGAAAAT    GATAAAAAG     GACTAATAGT    ATATTTGAT     TTTGATTTT     TGATTTTGA          60

TTTTGATTT     TTGATTTTG     ATTTTGATT     TCAAATAATA    CAAATTTATT    TACTTATTA         120

ATTGTTTGA     TCAATTATT     TTCTG                                                      145
```

PERIPLASMIC MEMBRANE-BOUND SYSTEM FOR DETECTING PROTEIN-PROTEIN INTERACTIONS

This is a continuation of application Ser. No. 08/121,201 filed Sep. 13, 1993, now U.S. Pat. No. 5,529,006, which is hereby incorporated by reference.

FIELD OF THE INVENTION

This invention relates to assays for protein—protein interactions, fusion proteins, and host cells modified to comprise such proteins.

BACKGROUND OF THE INVENTION

Information about the extracellular environment is communicated to the inside of a cell by so-called signal transduction systems. Schlessinger, J., TIBS 13: 443–7 (1988); Stock, J. B., et al., Microbiol. Rev. 53: 450–490 (1989). Several classes of signal transducers are able to "transmit" a signal without internalization of the primary signal. Such signal transmission may result from binding of a ligand to a membrane-bound receptor, inducing a conformational change in the receptor.

One such signal transducer is the toxR-ctx system in *Vibrio cholerae*. Ctx is the gene for cholera toxin. ToxR protein is a transmembrane protein with a DNA-binding domain at its amino terminus, a strongly hydrophobic transmembrane domain, and an environmentally regulated, dimer-forming domain at its carboxyl terminus. Miller, V. L., et al., Cell 48: 271–279 (1984). According to current beliefs, the hydrophobic transmembrane region directs the carboxyl terminus to the periplasm while the amino terminus remains in the cytoplasm. A change in osmolarity or temperature in the periplasm is believed to effect the capacity of the toxR protein to form dimers with its carboxyl terminus. The carboxyl dimers in turn modulate the ability of the amino terminus of toxR to bind to repetitive sequences in the ctx promoter and, thereby, modulate the ability of RNA polymerase to initiate transcription at the ctx promoter. Id.

To test the hypothesis that toxR protein is a membrane protein, Miller et al. fused toxR protein with alkaline phosphatase (phoA). Cell 48: 271–279 (1984). The phoA enzyme naturally exists as a dimer in the periplasm and the phoA-toxR fusion protein was constitutively functional with respect to both phosphatase activity and toxR activation of ctx. This result demonstrated that toxR was able to direct alkaline phosphatase to the periplasm where it was active, and that the dimerization capacity of alkaline phosphatase could direct the toxR protein to activate ctx transcription.

In a similar fusion experiment, Mekalanos et al. fused toxR to a phoA mutant that requires $Zn^{2+}$ for dimerization and activity (personal communication). This fusion protein's phosphatase activity was dependent on $Zn^{2+}$, as expected, but so also was ctx activation. This result is consistent with the signal transduction model for toxR action.

Chimeric signal transduction systems have been constructed in prokaryotic cells with different bacterial systems (Utsumi. J., et al., Science 245: 1246–1249), in tissue culture cells with different eukaryotic hormone receptors (Riedel, H., et al., EMBO J. 8: 2943–2954 (1989)), and in tissue culture cells with a bacterial aspartate binding domain and the insulin receptor (Moe, G. E., et al., Proc. Natl. Acad. Sci. 86: 5683–7 (1989)). To date, however, no such system has employed the toxR receptor for *V. cholerae*.

SUMMARY OF THE INVENTION

The present invention relates to host cells comprising (a) a transmembrane fusion protein having (i) a periplasmic dimerization domain (e.g., a ligand-binding domain) and (ii) a toxR region having a cytoplasmic toxR DNA-binding region and a hydrophobic toxR transmembrane region, and (b) a nucleic acid molecule having a reporter gene operatively linked to the ctx operon, wherein dimer formation, which may or may not involve ligand binding, is signaled by expression of the reporter gene.

The present invention also relates to the aforementioned fusion protein, a corresponding nucleic acid molecule, and a corresponding expression vector having an inducible promoter. Further, the invention includes a process for detecting dimerization (e.g., as a result of binding of a ligand) of a membrane-bound protein, which comprises treating a culture of the host cells of this invention with a ligand and screening for expression of the reporter gene.

The present invention can be used to generate a signal from a variety of ligand-binding domains. Presence of a chosen ligand can be indicated by antibiotic resistance or a simple colorimeteric test for production of an enzyme. The periplasmic regions of the transmembrane protein could include therapeutically relevant domains, so that biologically pertinent interactions can be indicated by a readily measurable signal. Such transmembrane fusion proteins should also contribute to our understanding of dimerization domains, ligand-binding domains, protein membrane-spanning sequences, and signal transduction.

BRIEF DESCRIPTION OF THE FIGURES

FIG. 1 is a schematic representation of the mechanism employed by the present invention. As shown in FIG. 1, ligand-binding protein LBP is located within cell inner membrane IM and outer membrane OM. When the level expression of the toxR protein reaches a certain critical level, dimerization will ensue. Alternatively when a ligand L binds to the ligand binding domain of a toxR fusion protein, it may cause dimerization. In either instance, the dimerization induces a conformational change in the cytoplasmic domain of the wild type or toxR fusion protein which induces binding to the promoter region p of the reporter gene r. This DNA binding allows the RNA polymerase to transcribe the reporter gene, thus signaling dimerization which may result from either the spontaneous or ligand induced capacity of the periplamic domain to asociate.

FIG. 3 shows the results for the wild-type toxR gene, the truncated toxR from pTOX5, and a toxR in-frame gene fusion. The fusion in the example is to the leucine zipper dimerization domain of the yeast GCN4 protein, a well-studied dimerization domain representing an important control. (A) Co-transfection with lacZ reporter gene. For plasmids pTOX3, pTOX5, and pTOX5GCN4, this figure shows the amount of β-galactosidase produced (measured in Miller units) in the presence of zero (first bar), 50 (second bar), and 200 (third bar) μM IPTG. These results show that β-galactosidase expression is dependent on the induction of the wild type toxR gene of pTOX3 by IPTG, and demonstrate that the truncated toxR product in pTOX5 fails to activate expression even following induction. The results noted for pTOX5-GCN4 demonstrate that a foreign dimerization domain can restore inducible activation. (B) Co-transfection with CAT reporter gene. The results given in part B show the activation of the chloramphenicol resistance gene from pCTX4 as expected for the strains expressing the wild-type toxR and chimeric toxR-GCN4. The amount of chloramphenicol used is noted at the top of each column in μg/mL. "J4" denotes the strain JM101 as transfected with pCTX4 "R" signifies chloramphenicol resistance; "S", sensitivity. Cells were grown in the presence of IPTG as noted in the materials and methods; when IPTG is omitted, chloramphenicol resistance is not observed.

DETAILED DESCRIPTION OF THE INVENTION

Figure 2A:
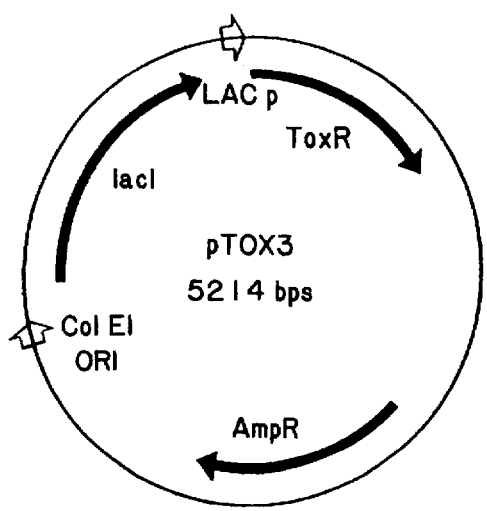
FIG. 2 shows control and fusion vectors. "LACp" denotes the lac promoter; "AmpR", the ampicillin resistance gene; "Spec", the spectinomycin resistance gene; "LacZ," the β-galactosidase gene; "CTXp", the cholera toxin promoter; "CAT", the chloramphenicol transferase gene. (A) pTOX3. This wild-type ToxR control vector includes a toxR PCR clone (SEQ. ID. NO. 1) from genomic *V. cholerae* in expression vector pSPORT1. The toxR gene is placed under the control of the lac promoter, making it inducible by treatment with IPTG. The desired transductants are selectable by treatment with ampicillin. The ColEI origin is compatible with the pSC101 origin. (B) pTOX5. This toxR fusion vector includes a truncated toxR PCR clone (SEQ. ID. NO. 2) from genomic *V. cholerae* in the vector pSPORT1. pTOX5 allows the in-frame cloning of foreign domains and may be used to generate families of fusions based on unidirectional deletion. The truncated pTOX5 does not activate the ctx promoter and any signals found in chimeric proteins result from the fused domain's capacity to dimerize. (C) pCTX3. This reporter gene vector includes the cholera toxin promoter, ctx (SEQ. ID. NO. 3), PCR-amplified from p3083 (Infection and Immunology, 58, pages 4142–4144, 1990) and cloned in a novel promoterless lacZ vector. This construct expresses β-galactosidase as a function of the dimerization of ToxR or ToxR fusion proteins. The pSC101 origin is compatible with the ColEI origin. The desired transformants may be selected by treatment with spectinomycin. (D) pCTX4. This vector includes a promoterless CAT gene from pCaMVCN inserted into the LacZ of pCTX3. Like the pCTX3 vector from which it is derived, pCTX4 also provides spectinomycin selection and expresses chloramphenicol acetyltransferase as a function of dimerization of toxR or toxR fusion proteins.
Figure 2B:
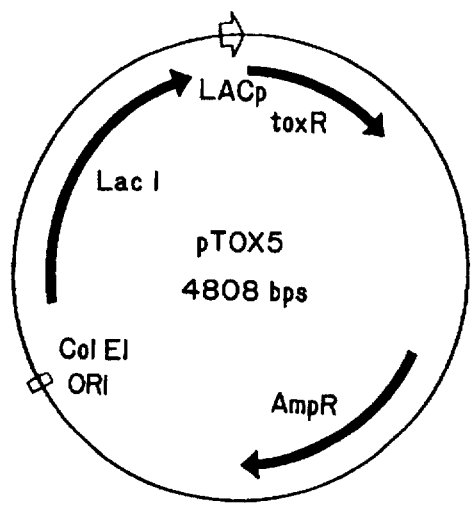
Figure 2C:
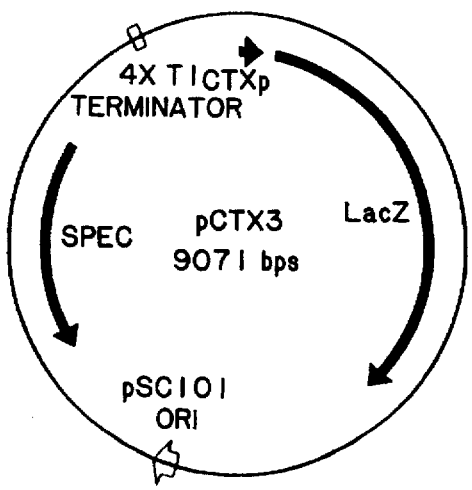
Figure 2D:
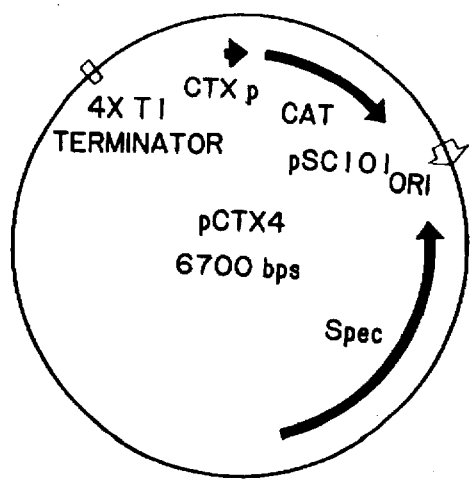

ToxR encodes a transmembrane protein possessing a DNA binding domain at its amino terminus. This intercellular domain has the capacity to activate expression from the ctx operon. Transactivation depends on the dimerization of toxR protein, which is directed by the protein's extracellular carboxyl domain. The toxR-ctx system can take the primary signal of protein-protein association and transduce it into the secondary message of gene expression. The natural membrane localization of the toxR protein, which is directed by its transmembrane segment, make it an attractive host for formation of chimera involving membrane proteins. This membrane confinement also has the intriguing feature of restricting protein diffusion to a 2-dimensional lipid plane. Placement of the dimerization domain in the extracellular periplasmic space will render it accessible to exogenous agents that might affect the dimer equilibrium.

Definition of terms

The following definitions apply to the terms as used throughout this specification, unless otherwise limited in specific instances.

The terms "dimerization domain" and "region capable of forming a dimer" refer to a polypeptide sequence capable of forming a self-dimer, either spontaneously or as a result of ligand binding and the like. Exemplary dimerization domains may be derived from trkC, GCN4, the HSV scaffold protein ICP35, HIV integrase, and the like.

The term "reporter gene" refers to any gene whose expression provides a measurable signal. Exemplary reporter genes include the genes for β-galactosidase and chloramphenicol transferase. Various other reporter genes are well known by those having ordinary skill in the art.

Process of preparation

Gene constructs

The nucleic acids used in the present invention may be prepared by recombinant nucleic acid methods. See, for example, the recombinant DNA methods of Nelles et al., *J. Biol. Chem.*, 262, 10855 (1987). Exemplary strains comprising such constructs are RFM2016 supE thi Δ(pro-lac) /F' (traD36 proAB+lac;$^Q$ lacZΔM15)/pTOX5/pCTX4 (ATCC Accession No. 69,403 ) and RFM2063 supE thi Δ(pro-lac) degP::Tn5/F' (traD36 proAB+lacI$^Q$ lacZΔM15)/ pTOX5trkC12/pCTX3 (ATCC Accession No. 69,404). ("ATCC" refers to the American Type Culture Collection, 12301 Parklawn Drive, Rockville, Md. 20852-1776.

The DNA sequences may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for the desired activity.

For cDNA, the cDNA may be cloned and the resulting clone screened with a probe for cDNA coding for the desired region. Upon isolation of the desired clone, the cDNA may be manipulated in substantially the same manner as the genomic DNA.

To express the DNA sequences, transcriptional and translational signals recognized by an appropriate host are necessary. It is preferred that the toxR gene sequence be operatively linked to an inducible promoter (e.g., the lac promoter), providing a control for the system.

Alternatively, the promoter region from genomic DNA may be obtained in association with the DNA sequence for the toxR or other region for the fusion protein. To the extent that the host cells recognize the transcriptional regulatory and translational initiation signals associated with the toxR region, the 5' region adjacent to the coding sequence may be retained and employed for transcriptional and translational regulation. This region typically will include those sequences involved with initiation of transcription and translation, such as the TATA box, capping sequence, CAAT sequence, and the like. Typically, this region will be at least about 150 base pairs long, more typically about 200 bp, and rarely exceeding about 1 to 2 kb.

The non-coding 3' region may be retained, as well, especially for its transcriptional termination regulatory sequences, such as the stop signal and polyadenylated region. In addition, the non-coding 3' region may also contain an enhancer. Where the transcriptional termination signals are not satisfactorily functional in the host cell, then a functional 3' region from a different gene may be substituted. In this method, the choice of the substituted 3' region would depend upon the cell system chosen for expression.

A wide variety of transcriptional and translational regulatory sequences may be employed, depending upon the nature of the host. The transcriptional and translational regulatory sequences may be derived from viral sources (e.g., adenovirus, bovine papilloma virus, Simian virus, and the like) where the regulatory signals are derived from a gene that has a high level of expression in the host. Alternatively, promoters from mammalian expression products (e.g., actin, collagen, myosin, and the like) may be employed. Transcriptional initiation regulatory signals may be selected that allow for repression or activation, so that expression of the genes can be modulated. One such controllable modulation technique is the use of regulatory signals that are temperature-sensitive, so that expression can be repressed or initiated by changing the temperature. Another controllable modulation technique is the use of regulatory signals that are sensitive to certain chemicals.

To form the toxR or ctx chimeric gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments.

The constructs for toxR and its fusion partner may be joined together to form a single DNA segment or may be maintained as separate segments by themselves or in conjunction with vectors. The constructs may be introduced into a cell by transformation in conjunction with a gene allowing for selection where the construct will become integrated into the host genome. Usually, the construct will be part of a vector having a replication system recognized by the host cell.

Expression vectors

Expression vehicles for production of the molecules of the invention include plasmids or other vectors. In general, such vectors contain control sequences that allow expression in various types of hosts, including but not limited to prokaryotes, yeasts, fungi, plants and higher eukaryotes. Suitable expression vectors containing the desired coding and control sequences may be constructed using standard recombinant DNA techniques known in the art, many of which are described in Sambrook, et al., *Molecular Cloning: A Laboratory Manual*, Second Edition, Cold Spring Harbor Laboratory, Cold Spring Habor, N.Y. (1989).

An expression vector as contemplated by the present invention is at least capable of directing the replication of the reporter gene construct and the replication and expression of the transmembrane fusion protein construct. One class of vectors utilizes DNA elements that provide autonomously replicating extrachromosomal plasmids derived from animal viruses (e.g., bovine papilloma virus, polyomavirus, adenovirus, or SV40). A second class of vectors relies upon the integration of the desired gene sequences into the host cell chromosome.

Expression vectors useful in the present invention typically contain an origin of replication, a promoter located 5' to (i.e., upstream of) the DNA sequence to be expressed, and a transcription termination sequence. Suitable origins of replication include, for example, the ColE1, pSC101, SV40 and M13 origins of replication. Suitable termination sequences include, for example, the bovine growth hormone, SV40, lacZ and AcMNPV polyhedral polyadenylation signals. Suitable promoters include, for example, the cytomegalovirus promoter, the lacZ promoter, the gal 10 promoter and the AcMNPV polyhedral promoter. The promoter sequence may also be inducible, to allow modulation of expression (e.g., by the presence or absence of nutrients or other inducers in the growth medium). One example is the lac operon obtained from bacteriophage lambda plac5, which can be induced by IPTG.

The expression vectors may also include other regulatory sequences for optimal expression of the desired product. Such sequences include stability leader sequences, which provide for stability of the expression product; secretory leader sequences, which provide for secretion of the expression product; enhancers, which upregulate the expression of the DNA sequence; and restriction enzyme recognition sequences, which provide sites for cleavage by restriction endonucleases. All of these materials are known in the art and are commercially available. See, for example, Okayama, *Mol. Cell. Biol.*, 3, 280 (1983).

A suitable expression vector may also include marking sequences, which allow phenotypic selection of transformed host cells. Such a marker may provide prototrophy to an auxotrophic host, biocide resistance (e.g., antibiotic resistance) and the like. The selectable marker gene can either be directly linked to the DNA gene sequences to be expressed, or introduced into the same cell by co-transfection. Examples of selectable markers include neomycin, ampicillin, hygromycin resistance and the like.

The characteristics of the actual expression vector used must be compatible with the host cell that is to be employed. For a mammalian host, for example, the expression vector may contain promoters isolated from the genome of mammalian cells, (e.g., mouse metallothionien promoter), or from viruses that grow in these cells (e.g., vaccinia virus 7.5K promoter).

Suitable commercially available expression vectors into which the DNA sequences of the present invention may be inserted include pSPORT (which is preferred), pBluescriptIISK, the mammalian expression vectors pcDNAI or pcDNA/Neo, the baculovirus expression vector pBlueBac, the prokaryotic expression vector pcDNAII and the yeast expression vector pYes2, all of which may be obtained from Invitrogen Corp., San Diego, Calif.

Host cells

The present invention additionally concerns host cells containing expression vectors that comprise DNA sequences for the toxR and ctx chimeric gene constructs.

Suitable host cells include both prokaryotic and eukaryotic cells. Suitable prokaryotic host cells include, for example, *E. coli* strains HB101, DH5a, XL1 Blue, Y1090 and JM101. Suitable eukaryotic host cells include, for example, *Spodoptera frugiperda* insect cells, COS-7 cells, human fibroblasts, and *Saccharomyces cerevisiae* cells.

Mammalian cells that may be useful as hosts include cells of fibroblast origin (e.g., VERO or CHO-K1) or lymphoid origin (e.g., SP2/0-AG14, or P3x63Sg8) or derivatives thereof. Preferred mammalian host cells include SP2/0 and J558L. Several cell lines secrete urokinase and may be used for transfection, such as cultured kidney carcinoma cells and 3T3 cells. Ferrivalo et al., *J. Cell Physiol.*, 121, 363 (1984); Belin et al., *EMBO J.*, 3, 190 (1984).

Another preferred host is yeast. Yeast provides substantial advantages in that it can also carry out post-translational peptide modification, including glycosylation. A number of recombinant DNA strategies exist that utilize strong promoter sequences and high copy number of plasmids that can be utilized for production of the desired proteins in yeast. Yeast recognizes leader sequences on cloned mammalian gene products and secretes peptides bearing leader sequences.

Immortalized cells, particularly myeloma or lymphoma cells, are also suitable host cells. These cells may be grown in an appropriate nutrient medium in culture flasks or injected into a synergenic host (e.g., mouse or rat) or an immunodeficient host or host site (e.g., nude mouse or hamster pouch). In particular, the cells may be introduced into the abdominal cavity for production of ascites fluid and harvesting of the chimeric molecule. Alternatively, the cells may be injected subcutaneously and the antibodies harvested from the blood of the host. The cells may be used in the same manner as the hybridoma cells. See Diamond et al., *N. Eng. J. Med.*, 304, 1344 (1981); *Monoclonal Antibodies: Hybridomas-A New Dimension in Biologic Analysis* (Kennatt, et al., eds.) Plenum (1980).

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Host cells containing an expression vector may be identified by one or more of the following six general approaches: (a) DNA—DNA hybridization; (b) the presence or absence of marker gene functions; (c) assessing the level of transcription as measured by the production of mRNA transcripts encoding the gene constructs in the host cell; (d) detection of the gene product immunologically; (e) enzyme assay; and (f) PCR.

In the first approach, the presence of a DNA sequence coding for the gene constructs can be detected by DNA—DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, etc.). A marker gene can be placed in the same plasmid as the fusion protein sequence or reporter construct under the regulation of the same or a different promoter or reporter. Expression of the marker gene indicates transfection of the vector having the DNA sequence for the fusion protein or reporter gene.

In the third approach, the production of mRNA transcripts encoding the fusion protein or reporter can be assessed by hybridization assays. For example, polyadenylated RNA can be isolated and analyzed by Northern blotting or a nuclease protection assay using a probe complementary to the RNA sequence. Alternatively, the total RNA of the host cell may be extracted and assayed for hybridization to such probes.

In the fourth approach, the expression of the fusion protein or reporter can be assessed immunologically, for example, by immunoblotting with antibody to the fusion protein or one of its regions (Western blotting). Alternatively, this technique could be carried out with the known epitope of the antibody variable region.

In the fifth approach, expression of the fusion protein or reporter can be measured by assaying for its activity (see below).

In the sixth approach, oligonucleotide primers homologous to sequences present in the expression system (i.e., expression vector sequences, fusion protein gene sequences, or reporter gene sequences) are used in a PCR to produce a DNA fragment of predicted length, indicating incorporation of the expression system in the host cell.

The expression vectors and DNA molecules of the present invention may also be sequenced. Various sequencing methods are known in the art. See, for example, the dideoxy chain termination method described in Sanger et al., *Proc. Natl. Acad. Sci. USA* 74, 5463–7 (1977), and the Maxam-Gilbert method described in *Proc. Natl. Acad. Sci USA* 74, 560–4 (1977).

Once an expression vector has been introduced into an appropriate host cell, the host cell may be cultured under conditions permitting expression of large amounts of the desired protein.

The fusion protein may be isolated and purified in accordance with conventional conditions, such as extraction, precipitation, chromatography, affinity chromatography, electrophoresis, and the like. The preferred method is affinity chromatography with either the amino terminal heptapeptide of the fibrin $\beta$ chain, which binds to the antifibrin site, or benzamidine, which binds to the plasminogen activator catalytic site.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope and spirit of the present invention.

Preferred Embodiments

Below are detailed descriptions of specific embodiments of the present invention. These embodiments are exemplary and serve to illustrate the broad applicability of the present invention.

The present inventors placed *V. cholerae's* full length toxR gene behind the inducible lac promoter of the vector pSPORT. This provides a control to characterize the behavior of this system in *E. coli*. To exploit this system, the inventors cloned a truncated toxR gene upstream of a multicloning site in the same parental vector (FIGS. 1 and 2).

TrkC Fusions

Figure 4:
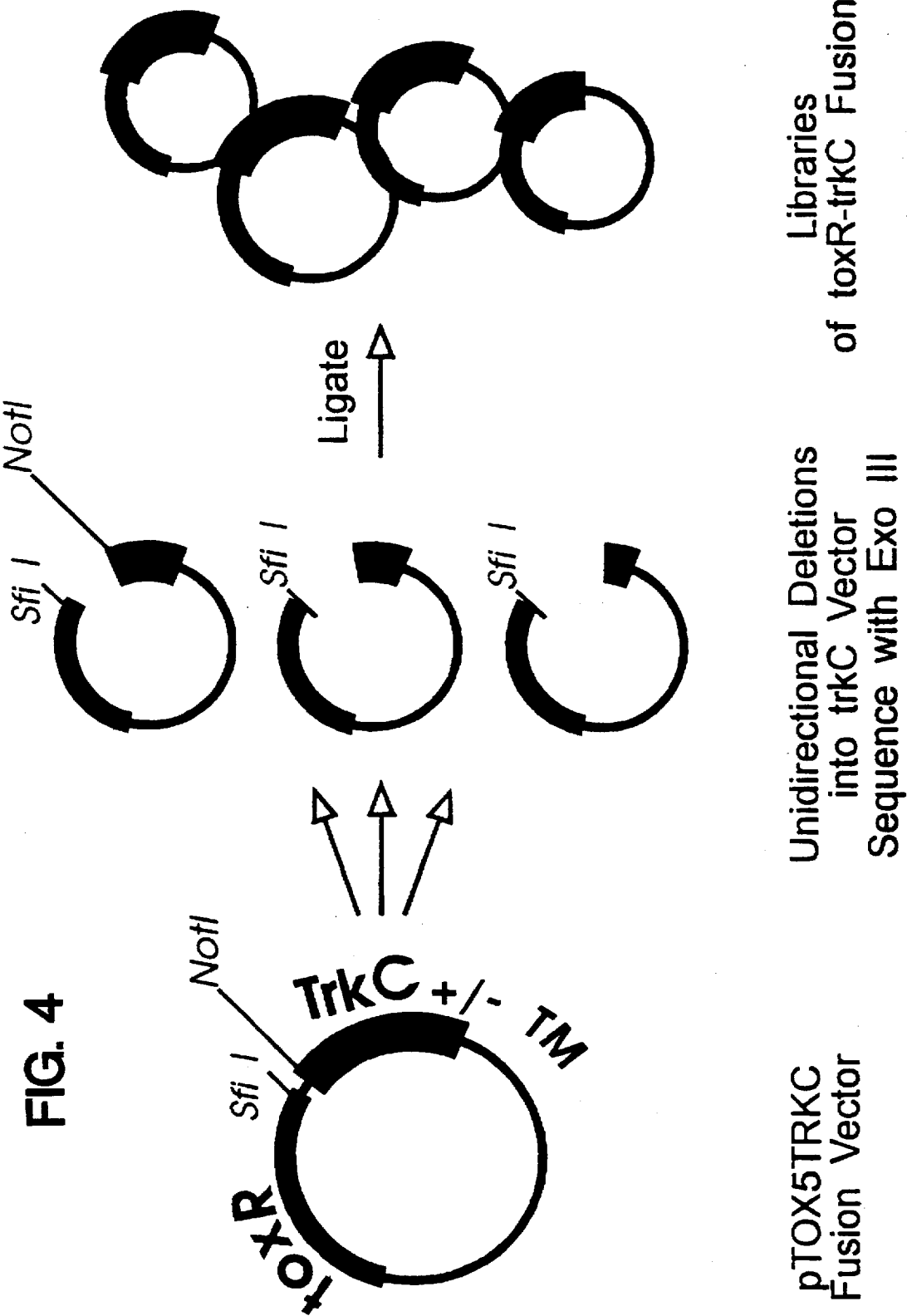
FIG. 4 shows a method for generating unidirectional deletions, as applied to a toxR-trkC fusion. TrkC is a member of the tyrosine kinase class of receptors and interacts with the nerve growth factor NT3 (*Cell*, 66, pages 967–979, 1991). A full length trkC cDNA clone was placed downstream of the truncated toxR gene in the fusion vector pTOX5 at the NotI cleavage site. Following digestion with SfiI and NotI, this vector was treated with exonuclease III (ExoIII), which provides 5'-to-3' directional deletions starting at the SfiI cleavage site. ExoIII-treated plasmids were subsequently digested with mung-bean nucleus. Upon ligation, this treatment results in a family of fusions between toxR and trkC segments of varying length.
Figures 5B, 5C:
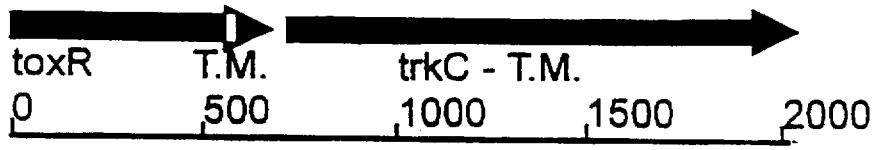
FIG. 5 shows the results for the toxR-trkC fusions prepared by the procedure of FIG. 4. (A). β-galactosidase assay. The toxR activity of various fusions was measured by β-galactosidase expression. Assays were performed in rich media (column LB) and minimal media (column min.) both in the presence of (100 μM) and absence of IPTG. (B) Sequencing of trkC portion. The table shown in part B reports the size (in base pairs) and the boundaries of the sequence deleted in the fusion as determined by comparing the sequence of the deletion mutant with that of the known trkC and toxR sequences. (C). Map of toxR-trkC fusions. The data in the table in part B is expressed graphically with the hollow boxes indicating the base pairs deleted in the indicated fusion.

ToxR-trkC fusions were prepared as described in FIG. 4. A large number of fusions with trkC segments of varying length were screened for toxR function (β-galactosidase activity at high IPTG in a host strain harboring the vector pCTX3). Clones with toxR activity were further characterized and the results are shown in FIG. 5.

These fusions demonstrate that the foreign trkC sequences (without their own transmembrane segment) are able to restore varying levels of toxR function, which is fusion-dependent.

Deletions that remove only small portions of trkC provide a fusion protein that demonstrates a toxR signal at higher levels of expression (high IPTG levels). In addition, a number of fusions that remove larger segments of trkC show enhanced dimer-forming ability, as demonstrated by toxR activity at low levels of expression (without IPTG.) In fact, many of the trkC fusions are more competent at ctx activation than is the wild type toxR protein with its own dimer forming domain. A possible model suggests that sequences in the wild-type trkC amino terminus obscure a very strong dimer forming capacity. In this model, NT3 binding in the wild type trkC protein might cause conformational changes that uncover this strong self-association domain.

The modified host cells allow a screen for trkC ligands with NT3-like activity, using chloramphenicol resistance or β-glactosidase as an indicator. Ligand activity will be signaled by the appearance of chloramphenicol resistance or β-glactosidase activity at a level of fusion expression below that which gives ligand-independent activity.

Other fusions

Figure 6A:
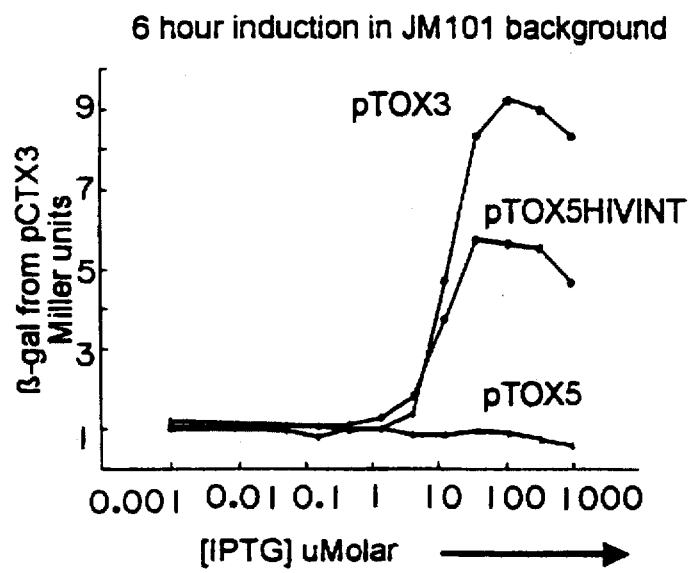
FIG. 6 shows the results obtained with fusions of HSV ICP35 and HIV integrase to the toxR deletion of pTOX5. (A,B) β-galactosidase activity induced by toxR fusions. The results for a six-hour induction in JM101 background (A) and for a four-hour induction in DH5a background (B) are shown. The y-axis shows β-galactosidase activity in Miller units; the x-axis, IPTG concentration in micromoles. These results confirm ctx activation by the toxR-viral fusion proteins and imply viral domain driven dimerization. (C) Chloramphenicol resistance induced by ToxR fusions. As in FIG. 3, dimerization is demonstrated by resistance to chloramphenicol, reported in μg/mL. "D4" refers to strain DH5α as a host strain and the remaining terms are as defined in FIG. 3.
Figure 6B:
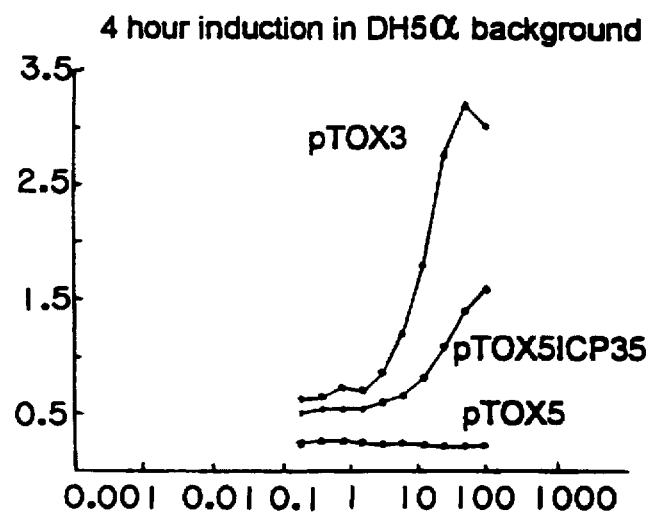

In addition to trkC and GCN4-directed toxR association, both the HSV scaffold protein ICP35 and the HIV integrase protein are competent to direct toxR function (see FIG. 6). Other suitable periplasmic binding regions for this invention include the bacterial chemotaxis receptors tar (aspartate) and tsr (serine), the human insulin receptor and HIV protease. All such fusions will allow screens to identify inhibitors specific to their respective fused dimerization domains.

Materials and methods

Strains

*Vibrio cholera* strain 569B rpf, classical biotype, Inaba serotype (courtesy of H.Smith) (BMS culture collection number SC15307) was used for all *V. cholera* DNA isolations.

*E. coli* strain JM101 (Messing 1979) was used in all ctx transactivation experiments. *E. coli* strains DH5α (Gibco-BRL) and JM101 were used for general plasmid maintenance and amplification.

Media

Vibrio strains were grown in NB (nutrient broth) supplemented with 0.5% NaCl at 30° C. *E. coli* strains were grown in LB (Luria-Bertani) broth at 37° C. When selection of plasmids was required, ampicillin was used at 50 µg/mL and spectinomycin was used at 50 µg/mL. Chloramphenicol was used at varying concentrations as described in the text.

Genetic techniques

Standard methods were used for the isolation and manipulation of plasmid DNA (Maniatis,T., Fritsch, E. F. & Sambrook, J.(1982) *Molecular Cloning: A Laboratory Manual* (Cold Spring Harbor Lab., Plainview, N.Y.). Genomic Vibrio DNA was prepared as described in Clark, J. M. & Switzer, R. L. (1977) *Experimental Biochemistry*, p. 230 (W. H. Freeman Co.,NY).

Unidirectional deletions were formed using ExoIII, mung bean nuclease, T4 DNA ligase from a unidirectional deletion kit (Stratagene) according to protocols supplied by the manufacturer. Briefly, the plasmid pTOX5TRKC was digested with SfiI and NotI restriction endonucleases prior to the addition of ExoIII. Aliquots were taken at one minute intervals for 5 minutes from the ExoIII mixture and the plasmid ends were flushed with mung bean nuclease and then ligated to create deletions into the trkC portion of the toxR-trkC chimera. These plasmids were transformed into JM101/pCTX3 (J3) and assayed for β-galactosidase as a measure of their ability to transactivate ctx-LACZ. Active fusions such as pTOX5TRKC Δ12 were then sequenced (B. Keinzle) on an ABI DNA sequencer to define the deletion endpoints and verify that an in-frame fusion was generated.

DNA was amplified by PCR using a Perkin-Elmer Cetus thermal DNA cycler 480 and GeneAmp DNA amplification kit. The reaction mix contained 1X Amplitaq Buffer with 1.5 mM magnesium chloride, 200 µM each dNTP, 2.5 U Amplitaq polymerase, 1.0 gM 5' and 3' primers and 10–100 ng template DNA in 100 µL total volume. In general, the amplification consisted of one cycle of 5 minutes at 94° C., 35 cycles consisting of one minute at 94° C. followed by 2 minutes at 52° C. then 3 minutes at 72° C. and completed with a final cycle of 8 minutes at 72° C. PCR products are analyzed on 0.8% agarose gels and then digested with restriction endonucleases (at sites engineered into the primers) prior to ligation into the host vector.

Standard methods were used for SDS-PAGE and immunoblotting of toxR fusion proteins (Maniatis, T., Fritsch, E. F. & Sambrook, J. (1982) *Molecular Cloning: A Laboratory Manual* (Cold Spring Harbor Lab., Plainview, N.Y.). Generally, whole cell protein or purified protein was loaded onto a 10% SDS Daiichi mini gel and electrophoresis was run at 40 mA constant current in 1X Laemmli buffer for one hour. Following electrophoresis, the proteins were transferred to a supported nitrocellulose membrane in a Hoeffer blotting tank for one to two hours at 375 mA constant current. Western analysis was conducted using a 1:1000 dilution of the primary antibody (rabbit anti-GSTTOX5 polyclonal sera) followed by a second incubation with a 1:3000 dilution of the secondary antibody (mouse or goat anti-rabbit monoclonal antibodies, BioRad) conjugated to alkaline phosphatase. The membrane was blocked with 5% powdered skim milk in Tris buffered saline (blotto) before the addition of the primary antibody and washed three times with blotto after the addition of each antibody. Antigenic proteins were visualized using the western blue stabilized substrate for alkaline phosphatase (Promega).

Plasmid Vectors pCTX3 and pCTX4. The plasmid pCTX3 was constructed by digesting pMLB1109 with PstI and BalI, and isolating the appropriate 5 kb fragment. This fragment was then ligated to a 5.7 Kb PstI and SmaI fragment of pMS421. The resulting plasmid, pCTX2, was partially digested with EcoRI to delete the 1.7 Kb lacI$^Q$ region. The EcoRI ends from the partial were filled in with Klenow polymerase and dNTPs, and then ligated to yield the vector pSLAC2. The plasmid pCTX3 was constructed by cloning an EcoRI-BmHI flanked PCR fragment of the CTX promoter from p3083 (R. Finklestein) into EcoRI and BamHI digested pSLAC2 to yield the 9.1 Kb plasmid. The plasmid pCTX4 was generated by inserting the BamHI and ClaI digested fragment of pCaMVCN (Pharmacia) containing the CAT gene into BamHI and ClaI digested pCTX3.

pTOX3, pTOX4, and pTOX5. The plasmid pTOX3 was constructed by PCR amplifying the toxR coding region with a 5' PstI restriction site containing PCR primer and a 3' SfiI restriction site harboring PCR primer using genomic DNA prepared from the *V. cholera* strain 569B rpf obtained from H. Smith. The resulting PCR fragment was cloned into PstI- and SfiI-digested pSPORT1 (BRL).

The plasmid pTOX4 was constructed by PCR amplifying, from genomic *V. cholera* DNA, the toxR coding region truncated at base pair 989 of the toxR reading frame using a PCR primer with a 5' PstI restriction site and a second primer with both a 3' SfiI restriction sites and stop codons. The resulting PCR fragment was cloned into PstI- and SfiI-digested pSPORT1 (BRL).

The plasmid pTOX5 was constructed by PCR amplifying a truncated version of the toxR coding region at base pair 827 of the toxR reading frame in a manner strictly analogous to that used in the pTOX4 construct.

pTOX51CP35. The plasmid pTOX51CP35 was developed by digesting pT71CP35K (L. Deckman) with KpnI and NcoI to yield a fragment containing the HSV ICP35 coding region. The NcoI site of this fragment was filled in with Taq polymerase and dNTPs. This modified insert was cloned into KpnI and StuI digested pTOX5 giving a fusion of the ICP35 reading frame aligned with that of the truncated toxR gene.

pTOX5TRKC+TM. The plasmid pTOX5TRKC+TM was constructed by generating a 1.3 kb PCR fragment of the trkC coding region from base pair position 32 to position 1391 of the trkC reading frame of pFL19 (M. Barbacid) containing 3' XbaI and 5' HindIII termini with stop codons derived from the PCR primers. This fragment was then cloned (not in-frame) into XbaI and HindIII digested pTOX5 to create a vector that could be used to make unidirectional deletions of trkC truncated just past the transmembrane domain fused to toxR.

pTOX5TRKC-TM. The plasmid pTOX5TRKC-TM was generated in the same fashion as pTOX5TRKC+TM, but the 1.3 kb PCR-generated (trkC position 32 to 1318) fragment did not contain the trkC transmembrane domain.

pTOX5TRKC-TM del 12. The plasmid pTOX5TRKC-TM Δ12 was created by treating with ExoIII the SfiI- and NotI-digested pTOX5TRKC-TM. ExoIII treatment was stopped at one-minute intervals, and mung bean nuclease was added to flush the ends prior to rejoining the plasmid deletions with T4 ligase. Deletion number 12 was sequenced and shown to be an in-frame deletion toxR-trkC segment of pTOX5TRKC-TM. The junction of the deletion contains the amino acid residues TG from the end of the truncated toxR gene with the intervening linker RSRSE joined to the initial methionine of the trkC sequence.

pTOX5HIVPROT. The plasmid pTOX5HIVPROT was devised from an SfiI-flanked 300-base pair PCR-amplified HIV Protease gene (P-F. Lin) cloned in-frame into SfiI-digested pTOX5.

pTOX5HIVINT. The plasmid pTOX5HIVINT was formulated by inserting an 896-base pair PCR product of the HIV integrase gene, with an SfiI site at the 5' terminus and XbaI site at the 3' terminus derived from the PCR primers (P-F. Lin), into SfiI and XbaI-digested pTOX5 to yield an in-frame fusion of the HIV integrase with toxR.

pTOX5GCN4. The plasmid pTOX5LINK was established to allow in-frame cloning of the leucine zippers of the yeast vesulatory protein GCN4 with SalI and BamHI termini. This vector was created by digesting pTOX5 with SfiI and BamHI, and cloning in two annealed oligonucleotides (sequences 5' to 3' GTCGACG and GATCCGTCGACCTC).

The plasmid pTOX5GCN4 was originated by liberating a 129-bp fragment from SalI- and BamHI-digested pJH370 (J. Hu) and cloning this piece into SalI- and BamHI-digested pTOX5LINK.

pTOX5LP19, pTOX5LV19, pTOX5LY19, pTOX5LI19, pTOX5LN19, pTOX5LK19. The plasmids pTOX5LP19, pTOX5LV19, pTOX5LY19, pTOX5LI19, pTOX5LN19, pTOX5LK19 were engineered identically to pTOX5GCN4 but included the SalI-BamHI fragments from pJH524, pJH505, pJH506, pJH518, pJH521, pJH528 (J. Hu) respectively.

pGSTTOX5. The plasmid pGSTTOX5 was made by digesting pGEX-3X (Pharmacia) with SmaI and BamHI and cloning in PCR amplified truncated toxR from pTOX5 with compatible ends.

Assays

β-galactosidase assays were performed essentially as described by Menzel (*Analytical Biochemistry* 181, p. 40–50 1989.)

Agar plate assays for ctx activation based on chloramphenicol resistance were performed with JM101 strains containing the plasmid pCTX4 and any of the following activating plasmids; pTOX3, pTOX5, pTOX5GCN4, pTOX51CP35, or pTOX5HIVINT. Overnight cultures were grown in LB with 100 μM IPTG. One to two microliters of the overnight culture was spotted on LB-agar plates with 100 μM IPTG and the levels of chloramphenicol indicated in the text. ToxR activity was scored based on the ability to grow on increasing levels of the drug. In the absence of IPTG, all strains failed to show any chloramphenicol resistance.

The abbreviations used in this specification are defined as follows.

| | |
|---|---|
| AcMNPV | *Autographa californica* multiple nuclear polyhedrosis virus |
| bp | base pairs |
| CAT | chloramphenicol transferase |
| cNDA | complementary DNA |
| DNA | deoxyribonucleic acid |
| HIV | human immunodeficiency virus |
| HSV | herpes simplex virus |
| IPTG | isopropylthiogalactoside |
| kb, kbp | kilobase pairs |
| NT | neurotrophin |
| PCR | polymerase chain reaction |
| phoA | alkaline phosphatase |
| RNA | ribonucleic acid |

What is claimed is:

1. A prokaryotic host cell comprising
   (a) a transmembrane fusion protein having
      (i) a toxR region having a toxR DNA-binding region and a toxR hydrophobic transmembrane region, and
      (ii) a periplasmic region capable of spontaneously forming a dimer; and
   (b) a nucleic acid molecule having a reporter gene operatively linked to the ctx operon;
wherein dimer formation is signaled by expression of the reporter gene.

2. A transmembrane fusion protein, comprising
   (a) a toxR region having a toxR DNA-binding region and a toxR hydrophobic transmembrane region, and
   (b) a region capable of spontaneously forming a dimer in the periplasm of a prokaryotic cell.

3. A nucleic acid molecule coding for the transmembrane fusion protein of claim 2.

4. An expression vector, comprising the nucleic acid of claim 3.

5. The host cell of claim 1, wherein the periplasmic region forms a dimer upon binding of a ligand.

6. A process for detecting inhibition of dimer formation among the periplasmic regions of claim 1, which comprises:
   (a) treating a culture of the host cells of claim 1 with a test substance, and
   (b) screening for expression of the reporter gene.

7. The host cell of claim 1, wherein the toxR region has the sequence of SEQ. ID. NO. 1.

8. The transmembrane fusion protein of claim 2, wherein the toxR region has the sequence of SEQ. ID. NO. 1.

9. The nucleic acid of claim 3, wherein the toxR region has the sequence of SEQ. ID. NO. 1.

10. The expression vector of claim 4, wherein the toxR region has the sequence of SEQ. ID. NO. 1.

11. The process of claim 6, wherein the toxR region has the sequence of SEQ. ID. NO. 1.

12. The nucleic acid of claim 3, wherein the toxR region has the nucleic acid sequence of SEQ. ID. NO. 2.

13. The expression vector of claim 4, wherein the toxR region has the nucleic acid sequence of SEQ. ID. NO. 2.

14. The process of claim 6, wherein the toxR region has the nucleic acid sequence of SEQ. ID. NO. 2.

15. The host cell of claim 1, wherein the periplasmic region comprises the dimer-forming region of GCN4.

16. The protein of claim 2, wherein the periplasmic region comprises the dimer-forming region of GCN4.

17. The nucleic acid of claim 3, wherein the periplasmic region comprises the dimer-forming region of GCN4.

18. The expression vector of claim 4, wherein the periplasmic region comprises the dimer-forming region of GCN4.

19. The process of claim 6, wherein the periplasmic region comprises the dimer-forming region of GCN4.

20. The host cell of claim 1, wherein the periplasmic region comprises the dimer-forming region of ICP35.

21. The protein of claim 2, wherein the periplasmic region comprises the dimer-forming region of ICP35.

22. The nucleic acid of claim 3, wherein the periplasmic region comprises the dimer-forming region of ICP35.

23. The expression vector of claim 4, wherein the periplasmic region comprises the dimer-forming region of ICP35.

24. The process of claim 6, wherein the periplasmic region comprises the dimer-forming region of ICP35.

25. The host cell of claim 1, wherein the periplasmic region comprises the dimer-forming region of HIV integrase.

26. The protein of claim 2, wherein the periplasmic region comprises the dimer-forming region of HIV integrase.

27. The nucleic acid of claim 3, wherein the periplasmic region comprises the dimer-forming region of HIV integrase.

28. The expression vector of claim 4, wherein the periplasmic region comprises the dimer-forming region of HIV integrase.

29. The process of claim 6, wherein the periplasmic region comprises the dimer-forming region of HIV integrase.

* * * * *